(12) United States Patent
Speck et al.

(10) Patent No.: US 9,216,273 B2
(45) Date of Patent: *Dec. 22, 2015

(54) MEDICAL DEVICE FOR DISPERSING MEDICAMENTS

(71) Applicant: Bayer Intellectual Property Gmbh, Monheim (DE)

(72) Inventors: Ulrich Speck, Berlin (DE); Bruno Scheller, Saarbrucken (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/257,070

(22) Filed: Apr. 21, 2014

(65) Prior Publication Data

US 2014/0228752 A1 Aug. 14, 2014

Related U.S. Application Data

(60) Continuation of application No. 13/866,547, filed on Apr. 19, 2013, which is a division of application No. 12/782,989, filed on May 19, 2010, now Pat. No. 8,439,868, which is a division of application No. 10/528,577, filed as application No. PCT/DE03/02871 on Aug. 26, 2003, now Pat. No. 8,257,305.

(30) Foreign Application Priority Data

Sep. 20, 2002 (DE) .................................. 102 44 847

(51) Int. Cl.
| | | |
|---|---|---|
| *A61M 25/10* | (2013.01) | |
| *A61L 29/08* | (2006.01) | |
| *A61L 29/16* | (2006.01) | |
| *A61L 31/16* | (2006.01) | |
| *A61L 31/08* | (2006.01) | |
| *A61M 25/00* | (2006.01) | |

(52) U.S. Cl.
CPC .......... *A61M 25/1002* (2013.01); *A61L 29/085* (2013.01); *A61L 29/16* (2013.01); *A61L 31/08* (2013.01); *A61L 31/16* (2013.01); *A61M 25/0045* (2013.01); *A61M 25/10* (2013.01); *A61M 25/1027* (2013.01); *A61L 2300/41* (2013.01); *A61L 2300/412* (2013.01); *A61L 2300/416* (2013.01); *A61L 2300/43* (2013.01); *A61M 25/104* (2013.01); *A61M 25/1038* (2013.01); *A61M 2025/0057* (2013.01); *A61M 2025/1004* (2013.01); *A61M 2025/105* (2013.01); *A61M 2025/1031* (2013.01); *A61M 2025/1075* (2013.01); *A61M 2025/1086* (2013.01)

(58) Field of Classification Search
CPC ................. A61M 2025/0062; A61M 25/0111; A61M 25/002; A61M 25/104; A61M 2025/1081; A61M 25/0045; A61M 25/1038; A61M 25/1002; A61M 25/1027; A61M 25/10; A61M 2025/1075; A61M 2025/0057; A61M 2025/1086; A61M 2025/1031; A61M 2025/105; A61L 29/085; A61L 29/16; A61L 2300/404; A61L 31/08; A61L 31/16; A61L 2300/43; A61L 2300/41; A61L 2300/412; A61F 2/958; C07D 305/14; A61K 9/1611; A61K 9/1623; A61K 9/1635; A61K 9/1694; A61K 31/337; A61K 31/335
USPC ............ 604/172, 265, 103.05, 103.14, 96.01, 604/101.01, 101.02, 101.03, 101.04, 604/101.05, 102.01–102.03, 915–919; 514/449; 424/422, 489, 426, 449; 606/191–194
See application file for complete search history.

(56) References Cited

U.S. PATENT DOCUMENTS

| | | | |
|---|---|---|---|
| 4,247,352 A | 1/1981 | Stupp et al. | |
| 5,049,131 A | 9/1991 | Deuss | |
| 5,092,841 A | 3/1992 | Spears | |
| 5,102,402 A | 4/1992 | Dror et al. | |
| 5,120,322 A | 6/1992 | Davis et al. | |
| 5,304,121 A | 4/1994 | Sahatjian | |
| 5,370,614 A | 12/1994 | Amundson et al. | |
| 5,490,839 A * | 2/1996 | Wang et al. | ............... 604/103.14 |
| 5,569,198 A | 10/1996 | Racchini | |
| 5,571,523 A | 11/1996 | Lee et al. | |
| 5,609,629 A | 3/1997 | Fearnot et al. | |
| 5,616,608 A | 4/1997 | Kinsella et al. | |
| 5,674,192 A | 10/1997 | Sahatjian et al. | |
| 5,716,981 A | 2/1998 | Hunter et al. | |

(Continued)

FOREIGN PATENT DOCUMENTS

| | | |
|---|---|---|
| DE | 101 15 740 A1 | 10/2002 |
| DE | 102 44 847 A1 | 4/2004 |

(Continued)

OTHER PUBLICATIONS

Axel et al., "Paclitaxel Inhibits Arterial Smooth Muscle Cell Proliferation and Migration In Vitro and In Vivo Using Local Drug Delivery," *Circulation,* 1997; 96:636-645.

(Continued)

*Primary Examiner* — Manuel Mendez

(57) ABSTRACT

For selective treatment of diseased tissue sections or organ parts, the surface of medical devices entering into contact with areas thereof under pressure is coated with lipophilic substantially water-insoluble medicaments binding to various tissue components with good adherence thereto, said medicaments having an effect thereupon a short time after entering into contact therewith without exerting a harmful influence upon adjacent healthy tissue.

10 Claims, No Drawings

(56) References Cited

U.S. PATENT DOCUMENTS

| | | | |
|---|---|---|---|
| 5,733,925 A | 3/1998 | Kunz et al. | |
| 5,766,158 A | 6/1998 | Opolski | |
| 5,814,301 A | 9/1998 | Klopp et al. | |
| 5,824,049 A | 10/1998 | Ragheb et al. | |
| 5,827,289 A | 10/1998 | Reiley et al. | |
| 5,843,089 A | 12/1998 | Sahatjian et al. | |
| 5,849,368 A | 12/1998 | Hostettler et al. | |
| 5,865,814 A | 2/1999 | Tuch | |
| 5,868,719 A | 2/1999 | Tsukernik | |
| 5,893,840 A | 4/1999 | Hull et al. | |
| 5,900,246 A | 5/1999 | Lambert | |
| 5,916,596 A | 6/1999 | Desai et al. | |
| 5,954,706 A | 9/1999 | Sahatjian | |
| 5,976,534 A | 11/1999 | Hart et al. | |
| 5,977,163 A * | 11/1999 | Li et al. | 514/449 |
| 5,980,972 A | 11/1999 | Ding | |
| 5,981,568 A | 11/1999 | Kunz et al. | |
| 5,985,307 A | 11/1999 | Hanson et al. | |
| 6,013,092 A | 1/2000 | Dehdashtian et al. | |
| 6,017,577 A | 1/2000 | Hostettler et al. | |
| 6,039,721 A | 3/2000 | Johnson et al. | |
| 6,071,285 A | 6/2000 | Lashinski et al. | |
| 6,129,705 A | 10/2000 | Grantz | |
| 6,146,358 A | 11/2000 | Rowe | |
| 6,280,411 B1 * | 8/2001 | Lennox | 604/103.05 |
| 6,287,285 B1 | 9/2001 | Michal et al. | |
| 6,306,166 B1 | 10/2001 | Barry et al. | |
| 6,364,856 B1 | 4/2002 | Ding et al. | |
| 6,369,039 B1 | 4/2002 | Palasis et al. | |
| 6,419,692 B1 | 7/2002 | Yang et al. | |
| 6,441,025 B2 * | 8/2002 | Li et al. | 514/449 |
| 6,491,617 B1 | 12/2002 | Ogle et al. | |
| 6,515,016 B2 | 2/2003 | Hunter | |
| 6,544,223 B1 | 4/2003 | Kokish | |
| 6,562,061 B1 | 5/2003 | Wang et al. | |
| 6,589,546 B2 | 7/2003 | Kamath et al. | |
| 6,610,317 B2 * | 8/2003 | Straub et al. | 424/422 |
| 6,616,650 B1 | 9/2003 | Rowe | |
| 6,638,246 B1 | 10/2003 | Naimark et al. | |
| 6,682,545 B1 | 1/2004 | Kester | |
| 6,918,927 B2 | 7/2005 | Bates et al. | |
| 6,939,320 B2 | 9/2005 | Lennox | |
| 8,257,305 B2 | 9/2012 | Speck et al. | |
| 8,439,868 B2 * | 5/2013 | Speck et al. | 604/103.02 |
| 2001/0037140 A1 | 11/2001 | Gaudoin et al. | |
| 2002/0098278 A1 | 7/2002 | Bates et al. | |
| 2002/0142050 A1 | 10/2002 | Straub et al. | |
| 2003/0059454 A1 | 3/2003 | Barry et al. | |
| 2003/0100600 A1 | 5/2003 | Kinsella et al. | |
| 2004/0047909 A1 | 3/2004 | Ragheb et al. | |
| 2004/0068241 A1 | 4/2004 | Fischer, Jr. | |
| 2008/0102033 A1 | 5/2008 | Speck et al. | |
| 2010/0189876 A1 | 7/2010 | Kokish et al. | |
| 2013/0231638 A1 | 9/2013 | Speck et al. | |

FOREIGN PATENT DOCUMENTS

| | | |
|---|---|---|
| EP | 0 975 340 B1 | 10/2004 |
| EP | 1 140 273 B1 | 6/2005 |
| EP | 1 666 071 B1 | 6/2006 |
| EP | 1 372 737 B1 | 8/2006 |
| EP | 1 666 070 B1 | 9/2007 |
| EP | 0 975 340 B2 | 10/2009 |
| WO | WO 92/11890 A1 | 7/1992 |
| WO | WO 92/11895 A1 | 7/1992 |
| WO | WO 94/23787 A1 | 10/1994 |
| WO | WO 96/25176 A1 | 8/1996 |
| WO | WO 96/39949 A1 | 12/1996 |
| WO | WO 96/39970 A1 | 12/1996 |
| WO | WO 97/41916 A1 | 11/1997 |
| WO | WO 98/14174 A1 | 4/1998 |
| WO | WO 98/30249 A2 | 7/1998 |
| WO | WO 98/36784 A1 | 8/1998 |
| WO | WO 98/30249 A3 | 9/1998 |
| WO | WO 98/43618 A2 | 10/1998 |
| WO | WO 98/51282 A1 | 11/1998 |
| WO | WO 99/08729 A1 | 2/1999 |
| WO | WO 99/08729 A1 | 5/1999 |
| WO | WO 99/25336 A1 | 5/1999 |
| WO | WO 99/45918 A1 | 9/1999 |
| WO | WO 99/49908 A1 | 10/1999 |
| WO | WO 00/10622 A1 | 3/2000 |
| WO | WO 00/12512 A1 | 3/2000 |
| WO | WO 00/21584 A1 | 4/2000 |
| WO | WO 00/32238 A1 | 6/2000 |
| WO | WO 00/32267 A2 | 6/2000 |
| WO | WO 00/44414 A1 | 8/2000 |
| WO | WO 00/45744 A1 | 8/2000 |
| WO | WO 00/32238 A1 | 12/2000 |
| WO | WO 01/24866 A1 | 4/2001 |
| WO | WO 01/49268 A1 | 7/2001 |
| WO | WO 00/44414 A1 | 11/2001 |
| WO | WO 02/076509 A2 | 10/2002 |
| WO | WO 03/026718 A1 | 4/2003 |
| WO | WO 2004/006976 A1 | 1/2004 |
| WO | WO 2004/028582 A1 | 4/2004 |
| WO | WO 2004/028610 A2 | 4/2004 |
| WO | WO 2004/028610 A3 | 6/2004 |
| WO | WO 2005/027996 A2 | 3/2005 |
| WO | WO 2005/027996 A3 | 6/2006 |

OTHER PUBLICATIONS

Baumbach et al., "Local Drug Delivery: Impact of Pressure, Substance Characteristics, and Stenting on Drug Transfer Into the Arterial Wall," *Catheterization and Cardiovascular Interventions*, 1999; 47:102-106.

Charles et al., "Ceramide-Coated Balloon Catheters Limit Neointimal Hyperplasia After Stretch Injury in Carotid Arteries," *Circulation Research*, 2000; 87:282-288.

Creel et al., "Arterial Paclitaxel Distribution and Deposition," *Circ. Res.*, 2000; 86:879-884.

Ettenson et al., "Local drug delivery: an emerging approach in the treatment of restenosis," *Vascular Medicine*, 2000; 5:97-102.

Gonschior, MD, "Local Drug Delivery for Restenosis and Thrombosis—Progress?" *J. Invasive Cardiol.*, 1998; 10:528-532.

Heldman et al., "Paclitaxel Stent Coating Inhibits Neointimal Hyperplasia at 4 Weeks in a Porcine Model of Coronary Restenosis," *Circulation*, 2001; 103:2289-2295.

Heldman et al., "Intercouncil Review: Animal Models of Vascular Disease: Restenosis and Remodeling," *Circulation*, 1997; 96(Suppl. I):I-288.

Herdeg et al., "Visualization and comparison of drug effects after local paclitaxel delivery with different catheter types," *Basic Res. Cardiol.*, 1999; 94:454-463.

Höfling et al., "Clinical Perspective—Intravascular local drug delivery after angioplasty,"*European Heart Journal*, 1995; 16:437-440.

Hou et al., "Intrapericardial Paclitaxel Delivery Inhibits Neointimal Proliferation and Promotes Arterial Enlargement After Porcine Coronary Overstrectch," *Circulation*, 2000;102:1575-1581.

Indolfi et al, "Smooth Muscle Cell Proliferation is Proportional to the Degree of Balloon Injury in a Rat Model of Angioplasty," *Circulation*, 1995; 92(5):1230-1235.

Kandarpa et al., "Mural Delivery of Iloprost with Use of Hydrogel-coated Balloon Catheters Suppresses Local Platelet Aggregation," *J. Vasc. Interv. Radiol.*, Nov.-Dec. 1997; 8(6):997-1004.

Kandarpa et al., "Site-specific Delivery of Iloprost during Experimental Angioplasty Suppresses Smooth Muscle Cell Proliferation," *J. Vasc. Interv. Radiol.*, May-Jun. 1998; 9:487-493.

Kolodgie et al., "Local Delivery of Ceramide for Restenosis—Is There a Future for Lipid Therapy?" *Circulation Research*, 2000; 87:264-267.

Li et al., "Synthesis, Biodistribution and Imaging Properties of Indium-111-DTPA-Paclitaxel in Mice Bearing Mammary Tumors," *J. Nucl. Med.*, 1997; 38(7):1042-1047.

Liggins et al., "Solid-State Characterization of Paclitaxel," *Journal of Pharmaceutical Sciences*, Dec. 1997; 86(12):1458-1463.

Makkar et al., "Prevention of Restenosis by Local Drug Delivery," *J. Cardiovasc. Pharmacol. Therapeut.*, 1996; 1(2):177-188.

(56) References Cited

OTHER PUBLICATIONS

Mitchel et al., "Inhibition of Platelet Deposition and Lysis of Intracoronary Thrombus During Balloon Angioplasty Using Urokinase-Coated Hydrogel Balloons," *Circulation*, Oct. 1994;. 90(4):1979-1988.

Oberhoff et al., "Local Delivery of Paclitaxel Using the Double-Balloon Perfusion Catheter Before Stenting in the Porcine Coronary Artery," *Catheterization and Cardiovascular Interventions*, 2001; 53:562-568.

Richey et al., "Surface modification of polyethylene balloon catheters for local drug delivery,"*Biomaterials*, 2000; 21:1057-1065.

Scott, "Current Status and Potential Applications of Drug Delivery Balloon Catheters," *Journal of Interventional Cardiology*, 1995; 8(4):406-419.

Sollott et al., "Taxol Inhibits Neointimal Smooth Muscle Cell Accumulation after Angioplasty in the Rat," *The Journal of Clinical Investigation*, Apr. 1995; 95:1869-1876.

Wilensky et al., "Methods and Devices for Local Drug Delivery in Coronary and Peripheral Arteries," *Trends Cardiovascular Medicine*, 1993; 3(5):163-170.

\* cited by examiner

MEDICAL DEVICE FOR DISPERSING MEDICAMENTS

This application is a continuation of U.S. application Ser. No. 13/866,547, filed on Apr. 19, 2013, which is a divisional of U.S. application Ser. No. 12/782,989, filed on May 19, 2010 (now U.S. Pat. No. 8,439,686), which is a divisional of U.S. application Ser. No. 10/528,577, filed on Mar. 21, 2005 (now U.S. Pat. No. 8,257,305), which is the national stage of PCT/DE2003/002871, filed on Aug. 26, 2003, all of which are incorporated herein by reference in their entireties.

This invention relates to a medical apparatus that releases drugs for the selective therapy of specific tissues or organ parts and to a method of manufacturing such drug-coated devices.

Numerous diseases do not affect the entire organism at the same time but are restricted to specific tissues, often even to very limited individual tissue areas or organ parts. Examples can be found among tumor, joint and vascular diseases.

Pharmacotherapy of such diseases generally is effected by oral or intravenous administration of drugs that spread throughout the body and cause undesirable side effects in healthy tissues and organs, especially when the disease to be treated is in a severe stage, which limit the therapeutic application. The diseased tissues could be treated either selectively using drugs that specifically bind to diseased tissue (e.g. antibodies) while the administration path is maintained, or by selective administration, e.g. direct injection into the diseased tissue or supply via a catheter to the blood vessels that feed the diseased tissue. In case of selective administration may problems arise due to the short period of time during which the drugs are efficacious and the invasive administration paths, as repeated administration is not an option. When drugs are selectively administered via the bloodstream that feeds the diseased tissue, there is the additional problem that the drugs are insufficiently extracted when the blood or active agent solution swiftly flows through the blood vessels.

These problems used to be addressed by various pharmaceutical preparations with sustained release of the active agent, drug-releasing implants or selective access paths that stay operational for a longer period of time such as implanted catheters, etc.

It is known that the surface of medical equipment inserted into the body, in particular, of catheters, can be coated with agents that enhance gliding quality or prevent blood coagulation but have no therapeutic effect.

In addition, catheters are equipped with special devices for injecting drugs into the arterial wall, for example, using needles or a perforation of the catheter wall that sits adjacent to the vessel wall and through which the drug is injected at high pressure.

Other principles are based on extending the contact time between the arterial wall and an active agent preparation administered via the catheter by either blocking the blood flow for a sufficient period of time, e. g. using dual balloon catheters in which the active agent solution is contained in a chamber between the balloons, or by voids between a toric outer wall of the balloon allowing a limited flow of blood through a canal that passes through the balloon.

According to U.S. Pat. No. 5,102,402, drugs in the form of microcapsules are inserted into preformed recesses of balloon catheters for delayed release of the active agent. When the balloon is inflated, the microcapsules are to be pressed against the vessel wall, remain there and slowly release the active agent(s). Many authors propose to apply drugs embedded in hydrogel onto balloon catheters while they do not specify the function of the hydrogel, i. e. to act as an adhesive, to improve the gliding quality, or for controlled drug release.

A disadvantage of the products mentioned above is their complex structure, which causes production, quality control, and cost problems and forces additional aggravating working steps on doctors and patients when applied. Some of the methods mentioned may result in undesirable vascular damage in excess of the intended dilatation of the vessel. Another setback is that each measure aimed at extending contact time entails another reduction in blood and oxygen supply to the downstream tissues.

For the sake of completeness, we also refer to a device for preventing restenosis as described in WO 01/24866 that is coated with a lipid ceramide substance derived from natural cell membranes. This substance is used because of its affinity to cell walls that is not found in common drugs. Experts in the field continue to state that restenosis prevention using drugs requires release of the active agent over a period of several days.

The problem underlying the present invention is to provide a device for the release of drugs into specific tissue areas or organ parts that has a strong therapeutic effect without damaging healthy tissue, which is sufficiently well tolerated, and can be produced and applied with a minimal effort.

This problem is solved according to the invention by a device designed or produced in accordance with the characteristics of claims 1 and 15. The subordinate claims disclose further characteristics and advantageous improvements of the invention.

The invention provides improved drug-carrying balloon catheters or similar medical devices manufactured in a simple process that are highly versatile and facilitate the immediate release of active agents. Surprisingly, and contrary to the currently acknowledged opinion, no continuing release of the active agent from an inert matrix (polymer, hydrogel, microcapsule, etc.) and no special chemical or physical state of the active ingredients is required or useful. Therefore, no sophisticated techniques for producing or controlling depot formulations are required.

Coating balloons on catheters with drugs according to this invention is particularly useful because there is a frequent need for treatment after blood vessels or other passages in the body were dilated with balloons to prevent stenosis or an occlusion of the lumen created by the pressure of the balloon, to limit tumor growth or to enhance healing processes including the formation of collateral circulation. This can be achieved by drugs that become effective in the immediate vicinity of the balloon surface. The drugs firmly adhere to the balloon while passing through arteries with an intense blood flow on their way to their target until the balloon is inflated, and an effective dose is released in the short time (sometimes just a few seconds) during which the inflated balloon is in contact with the tissue, absorbed by the tissue in such a way that the blood flow that resumes immediately after the balloon is deflated does not rinse it off.

The subjects for coating are wires of the invention used to guide catheters, needles and catheters or catheter parts that are pressed against the diseased tissue at least for a short time. Preferred catheter materials are polyamides, polyamide mixtures and copolymers, polyethylene terephthalate, polyethylene and copolymers, polyurethane, natural rubber and its derivatives. The lengths and diameters of the catheter or balloon areas designated for pharmacological treatment are not of any decisive importance for their application as the dosage is calculated in µg of active agent/mm$^2$ of surface area. For example, balloons with diameters ranging from 2 to 4 mm and lengths ranging from 1.0 to 4.0 cm are commonly used for coronary dilatation. Balloons up to >20 mm in diameter and up to >10 cm in length can be used for other vessels. The surfaces to be coated may be smooth (i.e. without a special structure for absorbing the active agents), roughed up or comprise any structure; while no special surface structures are required for the active agents to adhere, such structures also do not impede adhesion. Adhesion of the active agents to the balloon surfaces is exclusively caused by selecting suitable solvents and, optionally, adding substances that influence adhesion. It is even surprisingly strong on completely smooth balloon surfaces.

All surfaces can additionally be coated with substances that improve the gliding quality of the products, prevent blood from coagulating on the surface or improve any other properties of these medical products have but the materials used for coating do not have to be released into the environment and this additional coating does not noticeably reduce the release of the active agents for treatment of the target tissue and thus the product's efficacy.

Balloon catheters are formed by dilating a segment of 1 cm to ca. 10 cm length of very thin plastic tubes. The dilated, very thin-wailed balloon membrane is then folded several times along the catheter axis and wrapped tightly around the catheter axis so that the dilated area, when folded, is only slightly greater in diameter than the rest of the catheter. The tight folding of the balloon membrane is required for passing the balloon catheter through access ports, guiding catheters and heavily stenosed sections of blood vessels.

The balloons of catheters can be coated when folded or when unfolded. The process always provides an intact and sufficiently uniform surface coating, and the active agents adhere to the surface of the balloon catheter even when it is refolded after being coated when unfolded.

A balloon that was coated when unfolded is produced without any impact on the coating, for example by using balloon membranes with preformed folds and bends whose structure is not lost due to dilatation and which allow the balloon membrane to refold at least loosely when the pressure is discharged from the balloon without requiring an external force as primary cause. It is only after this prefolding that the preformed folds are compressed by external pressure or by a vacuum. Folds are in no way required to hold the active agent. In addition refolding can be achieved using minor mechanical force by very smooth materials, and the tools used may also be wetted by slippery biocompatible liquids in which the active ingredients do not or, at least, do not well dissolve.

In accordance with another variant of the invention, the balloons of readily folded balloon catheters are coated by dipping them into low-viscosity active agent solutions. Solvent and active agent penetrate into the extremely dense folds where they form a surprisingly uniform coat that contains a reproducible dose and is not damaged by any subsequent step. The solution or, after the solvent has dried, the coat that adheres to the outer surface may be left there or may be removed in another step so that only the active agent portion that sits inside the folds of the balloon is retained.

After coating, when the balloon is folded, a stent can be pulled over the balloon catheter and firmly pressed onto it. The only step still required is sterilization, e. g. using ethylene oxide.

The work cycle laid out like this is extremely simple, hardly susceptible to failures, and can be carried out even with mechanically, chemically and physically sensitive coating materials. It was found that coating using this method does not result in any undesirable loosening or sticking together of the folds and that the active agent applied in this way adheres firmly enough to not be rinsed off by the bloodstream but releases most of the active agent when the balloon is inflated in the target tissue.

Suitable drugs are lipophilic, mostly water-insoluble and strongly acting drugs that bind to any tissue components. Drugs are called lipophilic when their butanol to aqueous buffer solution (pH 7) distribution ratio is 0.5, preferably 1 and particularly preferred 5, or when their octanol to aqueous buffer solution (pH 7) distribution ratio is 1, preferably 10, and particularly preferred greater than 50. Alternatively, or in addition to this, the drugs should reversibly and/or irreversibly bond to cell components at percentages greater than 10%, preferably greater than 50%, and particularly preferred greater than 80%. Preferred are substances that inhibit cell proliferation or inflammatory processes, or antioxidants such as Paclitaxel and other taxanes, Rapamycin and related substances, tacrolimus and related substances, corticoids, sexual hormones (estrogen, estradiol, antiandrogens) and related substances, statins, epothilones, probucol, prostacyclins, angiogenesis inducers, etc.

These substances are preferably present as a dry solid or as an oil on the surfaces of the various medical products. Preferred are the smallest particle sizes (mostly <5 microns, preferably <1 microns, particularly preferred <0.1 microns), particularly preferred are amorphous non-crystalline structures of the finest particle size that dissolve fast upon contact with tissue due to their large surface area and despite the generally poor water-solubility of the drugs and do not function as microcapsules, i. e. dissolve spontaneously and fast. It is sufficient that an effective dose is present in the form of smallest or amorphous particles; larger particles hardly contribute to the active agent concentration in the tissue but do not cause any interference. The dosage depends on the desired effect and the efficacy of the drug used. It may be up to 5 $\mu g/mm^2$ and this value does not even constitute an upper limit. It is easier to handle smaller dosages.

Good adhesion to the surfaces of catheters, needles or wires on an improved absorption by the tissues is achieved by embedding strongly lipophilic active agents with poor water solubility in a readily water-soluble matrix substance. Suitable matrix substances are low-molecular (molecular weight <5000 D, preferably <2000 D) hydrophilic substances such as contrast agents and dyes used in vivo for various diagnostic procedures in medicine, sugar and related substances such as sugar alcohols, low-molecular polyethylene glycols, biocompatible organic and inorganic salts such as, for example, benzoates, salts and other derivatives of salicylic acid, etc. Examples of contrast agents are iodinated X-ray contrast agents and paramagnetic chelates, examples of dyes are indocyanine green, fluorescein, and methylene blue. Excipients may also improve shelf life of the products, cause specific additional pharmacological effects or be instrumental for quality control.

In another embodiment of the invention, the pharmaceutical active agents can be adsorbed to particles or applied to the surfaces of suitable medical products with a low-molecular matrix. Suitable particles once again are diagnostics known to be biocompatible such as ferrites and various contrast agents for sonography.

Excipients of any kind can be used at lower or higher doses than the active ingredients.

The medical products are coated using solutions, suspensions, or emulsions of the drugs and excipients mentioned above. Suitable media for solution, suspension or emulsion are, for example, ethanol, isopropanol, ethyl acetate, diethyl ether, acetone, dimethyl sulfoxide, dimethyl formamide, glycerin, water or mixtures thereof. Solvent selection is based on the solubility of the active agents and adjuvants, the wetting of the surfaces to be coated and the effect on the structure of the coating and particles remaining after evaporation of the solvent, their adhesion to the surface and active agent transfer to the tissue in very short contact times.

Coating can be carried out by immersing, spreading, applying with devices which deliver a defined volume to the surface or spraying at various temperatures and, optionally, vapor saturation of the solvents in the atmosphere. The procedure can be repeated several times using different solvents and excipients as may be required.

The balloons of folded balloon catheters ready for use can be given a surprisingly uniform, reproducible, dose-controllable coating without impairing catheter functionality by immersing them in solutions containing the active agent(s) or by other measures. When the balloons are repeatedly immersed in unsaturated active agent solutions, the active agent applied previously is not completely stripped off; instead, the active agent content of the balloons is increased in a reproducible manner.

Excess solution or excess substances from the coating solution that are loosely attached to the exterior can be removed with simple methods without impairing the efficacy of the coating.

The various types of medical devices designed and manufactured according to the invention come into short-term contact with the tissue, i. e. for a few seconds, minutes, or hours. It is desirable in some cases to pharmacologically treat the tissue with drugs in the immediate vicinity of the medical product, e. g. to prevent excess growth as a response to an injury or to reduce tumor growth, to enhance neovascularization or diminish inflammatory reactions. In all these cases, high local drug concentrations can be achieved for an astonishingly long time using the method described above. A major advantage is the extraordinary versatility of uses of the products and methods described.

A preferred application is to reduce hyperproliferation of vessel walls induced by dilatation with balloon catheters. This can be achieved when stents are implanted by coating these stents with drugs, but only for the vessel section covered by the stent. The coated balloon catheters also treat any areas at short distance in front of and lust behind the stent that need treatment, they can treat the section where a stent has been implanted without requiring another stent implantation and vessels in which no stent is to be or can be implanted. An advantage as compared to the stents that release a drug over a long period of time is improved healing and simultaneous good inhibition of hyperproliferation and a reduced risk of thrombosis.

Several embodiments of the invention will be described below with reference to examples regarding the coating of balloon catheters, adhesion of the coating in the bloodstream, restenosis inhibition and active agent content of the catheters.

EXAMPLE 1

Coating an Expanded Balloon Catheter with Paclitaxel in Ethyl Acetate

Balloon catheters made by BMT, Oberpfaffenhofen/Munich, Germany, product name Joker Lite, balloon dimensions 2.5 mm by 20 mm, are inflated to the maximum and immersed full length for 1 minute in ethyl acetate, 18.8 mg Paclitaxel per ml, +1% pharmaceutical olive oil, dried: Paclitaxel content 39 micrograms (after extraction with ethanol, HPLC).

EXAMPLE 2

Coating a Folded Balloon Catheter with Paclitaxel in Ethyl Acetate

Balloon catheters made by BMT, Oberpfaffenhofen/Munich, Germany, product name Joker Lite, balloon dimensions 2.5 mm by 20 mm, are immersed full length in folded condition for i minute in ethyl acetate, 18.8 mg Paclitaxel per ml,+1% pharmaceutical olive oil, and dried:

Paclitaxel content 69 micrograms.

EXAMPLE 3

Coating a Folded Balloon Catheter with Paclitaxel in Ethyl Acetate a) Balloon catheters made by EMT, Oberpfaffenhofen/Munich, Germany, product name Joker Lite, balloon dimensions 2.5 mm by 20 mm, are immersed full length in folded condition for 1 minute in ethyl acetate, 16.6 mg Paclitaxel per ml, and dried for 4 hours:
Paclitaxel content 54 micrograms.
b) Same procedure, but additional two times immersed for 5 seconds with 1 hour drying time after each immersion process in solution A (=3.33 ml ethyl acetate+100.0 mg of Paclitaxel): Paclitaxel content 126 micrograms.
c) Same procedure, but additional four times immersed for 5 seconds with 1 hour drying time after each immersion process in the same solution:
Paclitaxel content 158 micrograms.

EXAMPLE 4

Coating a Balloon Catheter with Paclitaxel in Acetone

Dissolve 350 mg of Paclitaxel in 9.0 ml of acetone; balloon catheters made by BMT, Oberpfaffenhofen/Munich, Germany, product name Joker Lite, balloon dimensions 2.5 mm by 20 mm, are inflated to the maximum and immersed full length for 1 minute and removed. The solvent is dried for 12 hours at room temperature. Then the balloon is deflated and folded in the common way using a PTFE-coated tool. Optionally, one can crimp a stent of suitable dimensions onto the balloon: 29 micrograms of Paclitaxel on the balloon.

EXAMPLE 5

Coating a Balloon Catheter with Paclitaxel in Acetone
a) Immersion of folded balloon catheters made by SMT, product name Allegro, balloon dimensions 2.5 by 20 mm in a mixture of 0.15 ml ethanol+4.5 µl of Ultravist 300 (an X-ray contrast agent made by Schering AG, Berlin, Germany)+1.35 ml of acetone+0.8 mg of Sudan red+30.0 mg of Paclitaxel:
The folded balloon sections of the catheters are immersed 5 times, the first time for one minute, then dried for 3 hours, then 4 times at 1 hour intervals for 5 seconds each; subsequently, a stent was crimped on and the catheter was sterilized in the common way using ethylene oxide: Paclitaxel content 172 micrograms, no decomposition products of the active agent were determined using HPLC
b) A saturated aqueous mannitol solution is used instead of Ultravist 300
c) A saturated aqueous sodium salicylate solution (pH 7.5) is used instead of Ultravist 300
d) 5 my of acetylsalicylic acid are added to the completed solution according to (5a).
e) 5 mg of glycerin are added to the completed solution according to (5a).

EXAMPLE 6

Adhesion of the Active Agent in the Bloodstream 12 balloon catheters made by BMT, product name Allegro, balloon dimensions 2.5 by 20 mm, were used. The folded balloon sections of 6 catheters each were either 5 times immersed in [0.15 ml of ethanol+4.5 μl of Ultravist 300+1.35 ml of acetone+0.8 mg of Sudan red+30.0 mg Paclitaxel] or 5 times in [1.5 ml of ethyl acetate+0.8 mg Sudan red+31.0 mg Paclitaxel], the first time for 1 minute each with 3 hours of drying time, then 4 times for 5 seconds each at 1 hour intervals; then 3 of the folded balloons of each group were gently moved for 5 minutes at 37° C. in 50 ml of human blood and removed to determine the Paclitaxel content: Reduction of mean values (n=3 per coating method) by 5 minutes of movement in blood as compared to 3 control catheters that were not incubated in blood.

Acetone: 12%
Ethyl acetate: 10%

EXAMPLE 7

Examination of Restenosis Inhibition After Angioplasty and Stent Implantation in Coronary Arteries of Pigs Folded balloon catheters of the Joker Lite type made by BMT, 3.5 by 20 mm or 3.0 by 20 mm were immersed for 1 minute either in solution A) 3.33 ml of ethyl acetate (EA)+100.0 mg of Paclitaxel, or in solution B) 0.45 ml of ethanol+100 μl of Ultravist-370+4.5 ml acetone (ac)+150.0 mg Paclitaxel and dried over night at room temperature. One more (low dose=L) or 4 more (high dose=H) immersion process(es), respectively, were carried out for just five seconds at 1 hour intervals on the next day.

Active agent content after 2 immersions in solution (B) averaged 250 μg, after 5 immersions in solution (B) 500 μg, in solution (A) 400 μg.

The catheters coated with Paclitaxel or uncoated were used to implant stents into the left anterior or lateral coronary artery of a total of 22 pigs, and the vessels were slightly overdilated to stimulate restenosis by tissue hyperplasia. The animals were reangiographed after 5 weeks, and the vessel stenosis shown in the angiograms was measured using an automatic computer program.

| Group | Stenosis (%) |
|---|---|
| Uncoated | 50.49 |
| AcL | 20.22 |
| EAH | 36.01 |
| AcH | 0.86 |
| P | .004 |

Quantitative coronary angiography 5 weeks after stent implantation with uncoated and coated catheters; stenosis =reduction of lumen diameter in percent in the area of the stent as compared to the lumen diameter immediately after stent implantation; mean value and statistical significance of the effect of treatment.

EXAMPLE 8

Active Agent Content of the Catheters After Vessel Dilatation and Stent Implantation After stent implantation and removal from the animals, the balloons from Example 8 ca. 3 cm in length were cut off the balloon catheters and placed in 1.5 ml of ethanol. Paclitaxel content was determined using HPLC. All available coated balloons and a selection of uncoated balloons were examined.

Coronary,

| | | |
|---|---|---|
| 3.0 by 20 mm, coating: | Ac high | 38 ± 4 μg (n = 4) |
| | Ac low | 22 ± 5 μg (n = 2) |
| | EEE high | 41 (n = 1) |
| 3.5 by 20 mm, coating: | Ac high | 37 ± 10 μg (n = 8) |
| | Ac low | 26 ± 6 μg (n = 8) |
| | EEE high | 53 ± 9 μg (n = 9) |
| Uncoated (independent of size and vessel area) | | 0.9 ± 1.0 μg (n = 7) |

It follows from Example 6 that a maximum of 10% of the dose is lost before the balloon is inflated and about 10% of the dose remain on the balloon.

EXAMPLE 9

Probucol is added to acetone at a concentration of 100 mg per ml; the solution is used to coat balloon catheters as described in the above examples.

EXAMPLE 10

Rapamycin is dissolved at a concentration of 10 mg/ml in diethyl ether. The balloon sections of the catheters are coated as described in the above examples; after removal from the coating solution, the balloons should be brought into a horizontal position and continuously be turned around their longitudinal axis as soon as possible.

EXAMPLE 11

Epothilone B is dissolved in ethyl acetate at a concentration of 2 mg/ml; the solution is used to coat balloon catheters as described in the above examples.

The invention claimed is:

1. A medical device comprising a balloon having a balloon surface comprising paclitaxel and an inert matrix comprising a low molecular weight polyethylene glycol on the balloon surface.

2. The medical device of claim 1 wherein said medical device further comprises a stent.

3. The medical device of claim 1 wherein the balloon surface has preformed longitudinal folds maintaining an inclination to refold after inflation.

4. The medical device of claim 3 wherein at least an area covered by the folds is covered with the paclitaxel and polyethylene glycol.

5. The medical device of claim 3 wherein only an area covered by the folds is covered with the paclitaxel and polyethylene glycol.

6. The medical device of claim 1 wherein the balloon surface consists of a material to which the paclitaxel and low molecular weight polyethylene glycol adhere sufficiently well to resist forces required for folding, essentially without damage.

7. The medical device of claim 1 wherein the paclitaxel and low molecular weight polyethylene glycol are present as a dry solid on the balloon surface.

8. The medical device of claim 1 wherein the concentration of paclitaxel on said surface is up to 5 μmm$^2$.

9. The medical device of claim 1 wherein the polyethylene glycol has a molecular weight of less than 5000 D.

10. The medical device of claim 9 wherein the polyethylene glycol has a molecular weight of less than 2000 D.

* * * * *